(12) United States Patent
Tom-Moy et al.

(10) Patent No.: US 6,723,516 B1
(45) Date of Patent: Apr. 20, 2004

(54) METHOD FOR CONTINUOUSLY DETECTING THE PRESENCE AND QUANTITY OF ANALYTES IN A FLOWING LIQUID STREAM

(75) Inventors: May Tom-Moy, San Carlos, CA (US); Thomas P. Doherty, San Mateo, CA (US); Richard L. Baer, Los Altos, CA (US); Darlene J. Spira-Solomon, Portola Valley, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 1,889 days.

(21) Appl. No.: 08/738,464

(22) Filed: Oct. 24, 1996

Related U.S. Application Data

(63) Continuation of application No. 08/381,663, filed on Jan. 31, 1995, now abandoned.

(51) Int. Cl.$^7$ .................... G01N 33/53; G01N 33/557; G01N 27/00
(52) U.S. Cl. .................. 435/7.1; 435/6; 435/7.5; 435/969; 422/82.01; 422/98; 436/517; 436/518; 436/161
(58) Field of Search ..................... 422/62, 82, 82.11, 422/82.01, 90, 93, 98; 435/6, 7.5, 969; 436/517, 518, 524, 529, 527, 43, 52, 53, 161

(56) References Cited

U.S. PATENT DOCUMENTS

| | | | | |
|---|---|---|---|---|
| 4,283,201 A | * | 8/1981 | DeFord et al. | 23/230 |
| 5,130,257 A | | 7/1992 | Baer et al. | 436/151 |
| 5,156,972 A | * | 10/1992 | Issachar | 45/35 |
| 5,180,828 A | * | 1/1993 | Ghazarossian | 546/37 |
| 5,183,740 A | * | 2/1993 | Ligler et al. | 435/7.32 |
| 5,306,644 A | | 4/1994 | Myerholtz et al. | 436/149 |

FOREIGN PATENT DOCUMENTS

EP 416730 3/1991

OTHER PUBLICATIONS

U.S. patent application Ser. No. 08/167,273, Tom–Moy et al., filed Dec. 13, 1993.

* cited by examiner

*Primary Examiner*—Ponnathapu Achutamurthy

(57) ABSTRACT

A method is provided for continuously monitoring for the presence or quantity of an analyte in a flowing liquid stream. The method involves binding an analyte-specific receptor species to the surface of a piezoelectric substrate, contacting the surface bound receptor species with the flowing liquid stream and quantitating the presence of the analyte. A novel apparatus for detecting the presence of an analyte in a liquid chromatography eluant is provided as well.

14 Claims, 8 Drawing Sheets

METHOD FOR CONTINUOUSLY DETECTING THE PRESENCE AND QUANTITY OF ANALYTES IN A FLOWING LIQUID STREAM

CROSS REFERENCE TO RELATED APPLICATION(S)

This is a continuation of application Ser. No. 08/381,663 filed on Jan. 31, 1995, now abandoned.

TECHNICAL FIELD

The present invention relates generally to chemical methods for detecting preselected analytes in a flowing liquid stream. More specifically, the invention relates to a novel method for continuously monitoring the eluant from a liquid chromatography system so as to enable detection and quantitation of an analyte or analytes contained therein.

BACKGROUND

Processing biological materials often involves the use of liquid chromatography to separate and harvest a cellular product or metabolite of interest from cellular debris or cell media in a fermentation vessel. Typically, extracting the product of interest is accomplished using a series of chromatographic separations. In general, the chromatographic eluant is monitored using an ultraviolet-visible (UV-VIS) light-range spectrophotometer, and fractions which are thought to contain the product of interest are collected and pooled. These pooled fractions are further analyzed using any of a variety of biochemical analyses, such as Western blotting, SDS-PAGE, ELISAS, protein sequencing, or the like, in order to, first, determine if they correspond to the presence of the target analyte and, second, quantitate the analyte identified. The use of such a procedure to harvest a cellular product of interest, using well-known and characterized process steps, is time consuming and costly in terms of labor and production. In addition, the development of new process methodologies for separating and harvesting new compounds is compromised by the relatively slow process of resolving and identifying the specific compounds.

Previous attempts to develop post-column on-line detectors have been directed at analytical liquid chromatography and not preparative chromatography. In general, such detectors consist of two cells. The first cell is an enzyme reactor-detector in which a specific enzyme, for which the substrate is the target analyte, is immobilized on a solid-phase support. An enzyme-catalyzed reaction proceeds within this enzyme reactor cell between the immobilized enzyme and the substrate contained in the chromatography eluant, thereby generating an electroactive species such as hydrogen peroxide. The electroactive species is then detected in a second reactor cell which contains, for example, an electrochemical detector which makes an amperometric determination of the electroactive species. Thus, the immobilized enzyme contained in the first cell may be one or more of any number of specific oxidases which react with sugars, acids or alcohols to generate hydrogen peroxide.

Such a detection system utilizes both the specificity of immobilized enzymes and the high sensitivity of electrochemical detection; however, this system has certain deficiencies. For example, such a configuration requires the eluant to flow into two cells rather than one cell. In addition, the detection of the target analyte is indirect since it is based on the generation of an electroactive species which in turn is a product of the reaction between the target analyte and the enzyme. Non-specific electrochemical signals, i.e., background noise, may be generated by other cellular or media components which are capable of eliciting an amperometric response. The incorporation of an enzyme in the first cell dictates that special buffers must be used.

Moreover, users of the combined enzyme-electrochemical detection system are faced with a limited number and availability of useful enzymes. Such restricted availability of enzymes with desired specificities constrains this mode of detection with respect to the number and type of analytes that can be detected. Furthermore, the enzyme-catalyzed reaction must generate a species that is electroactive. In general, the time required for the analyte to react with the enzyme and then generate the electroactive species is on the order of minutes.

In other systems where enzymes are not utilized, the detection cell often incorporates an immobilized protein which binds to the target compound. However, in order to detect that binding event a secondary label, such as a fluorescently labeled antibody or antigen, is introduced. Such systems are usually not coupled with preparative chromatography systems as the target analyte is chemically altered by the fluorescent tag. In addition, as in the enzyme reactor detectors, these measurements are not made on a continuous basis.

Mass biosensors have been used to measure microquantities of biological materials, and involve the use of a modified surface which selectively binds a particular component. As explained in commonly assigned U.S. Pat. No. 5,130,257 to Baer et al., European Patent Publication No. 416,730 (inventors Tom-Moy et al.), U.S. Pat. No. 5,306,644 to Myerholz et al. and co-pending U.S. patent application Ser. No. 08/167,273, filed Dec. 13, 1993 (entitled "Method and Reagents for Binding Chemical Analytes to a Substrate Surface, and Related Analytical Devices and Diagnostic Techniques," inventors Tom-Moy et al.), a preferred type of mass biosensor uses a piezoelectric crystal as an acoustic waveguide. These sensors operate on the principle that changes in the amount of mass attached to their surface cause shifts in the resonant frequency. A typical device is constructed on a piezoelectric substrate and has interdigital input and output transducers defined by precise electrode fingers. Selective mass detection with such devices is achieved by coating the surface of the device with a chemically reactive layer that preferentially reacts with the substance to be detected, such that the mass present on the reactive layer changes proportionately, i.e., relative to the amount of the substance to be detected. These devices thus function as chemical sensors that can measure the concentration of analytes in a solution.

For example, and as explained in U.S. Pat. No. 5,306,644 cited above, piezoelectric surface wave devices have been used to measure the concentration of a specific antigen in solution using a conventional assay format, as follows. The mass-sensitive surface of the device is coated with a receptor layer which contains the antibody corresponding to the antigen, thereby forming a sample-sensing device. A reference device is also used which does not contain the antibody in the receptor layer. The devices are then exposed to a sample solution, and antigen present in the solution will bind to the receptor layer of the sample-sensing device, thereby increasing the mass loading of the surface. Radio frequency energy coupled into the device through an input transducer, such as an interdigital transducer (IDT), is converted to a surface acoustic wave confined to within about a few wavelengths of the surface. The velocity of the surface acoustic wave will vary according to the mass loading on the top surface of the device. The surface acoustic wave propagates along the surface of the device until it encounters the output transducer, such as an IDT, which converts the surface acoustic wave back into radio frequency energy. The change in propagation velocity of the surface acoustic wave corresponds to the mass bound to the surface of the crystal. The output frequency is converted to a voltage which is proportional to the phase difference between sample and reference devices. Such acoustic waveguide devices can utilize different wave motions, including surface transverse waves (STWs), Rayleigh waves (SAWs), Lamb waves, and surface-skimming bulk waves (SSBWs), although STW devices are preferred.

The present invention addresses the deficiencies in the art described above by providing a method for detecting a specific product in the eluant of a liquid chromatography system. The method employs a piezoelectric mass biosensor for continuous on-line monitoring of preselected analytes in a flowing liquid stream.

SUMMARY OF THE INVENTION

The present invention provides a method which yields accurate detection and quantitation of an analyte or multiple analytes in a flowing liquid stream, wherein the flowing liquid stream is obtained from any means by which constituents of a mixture are resolved to provide analytes of increased purity, for example, a liquid chromatography eluant.

The method and system described herein encompasses both the use of single and multiple piezoelectric surface wave sample devices for detecting and quantitating single or multiple analytes.

Accordingly, the present invention is directed to a method for continuously determining the presence or quantity of a preselected analyte in a flowing liquid stream which contains or is suspected of containing the analyte, which method comprises:

(a) contacting the flowing liquid stream with a system which comprises:

(i) a piezoelectric surface wave sample device comprising a receptor layer attached to the surface thereof containing receptor species complementary to the analyte and which device generates data relating to the mass change on the surface of the device arising from contacting the device with the flowing liquid stream; and (ii) a piezoelectric surface wave reference device comprising a receptor layer having little or no affinity for said analyte and which generates data as to the interference arising from contacting the device with the flowing liquid stream;

(b) obtaining data from both the sample and reference devices; and (c) determining the presence or quantity of the analyte in the liquid sample.

In another aspect of the invention, a liquid chromatographic system is provided for detecting the presence or quantity of a preselected analyte in a liquid sample comprising a liquid chromatography column in divertable fluid communication with (a) a means for introducing the sample onto the liquid chromatography column, (b) a means for eluting the sample from the column and (c) a detection means for determining the presence or quantity of the analyte in a flowing liquid stream, which detection means comprises a piezoelectric surface wave sample device and a piezoelectric surface wave reference device.

BRIEF DESCRIPTION OF THE FIGURES

FIG. 3a is a "sensorgram" of the signal from the STW sensor produced in response to the eluant from a chromatography column to which had been applied 45 µl of 1 mg/ml human immunoglobulin G. FIG. 3b is an overlay of the derivative of the signal shown in the sensorgram of FIGS. 3a with the corresponding chromatogram from a UV monitor. The dotted line represents the UV signal and the solid line is the derivative of the signal depicted in FIG. 3a.

FIG. 4a depicts a sensorgram of the eluant from a column to which had been applied 45 µl of 10% fetal bovine serum (FBS) in 20 mM sodium acetate. FIG. 4b depicts a sensorgram of the eluant from a column to which had been applied 45 µl of 1 mg/ml human immunoglobulin G (HIgG) in 10% FBS. FIG. 4c depicts a sensorgram of the eluant from a column to which had been applied 45 µl of 500 µg/ml HIgG in FBS. FIG. 4d depicts a sensorgram of the eluant from a column to which had been applied 45 µl of 100 µg/ml HIgG in FBS.

DETAILED DESCRIPTION OF THE INVENTION

Figure 1:
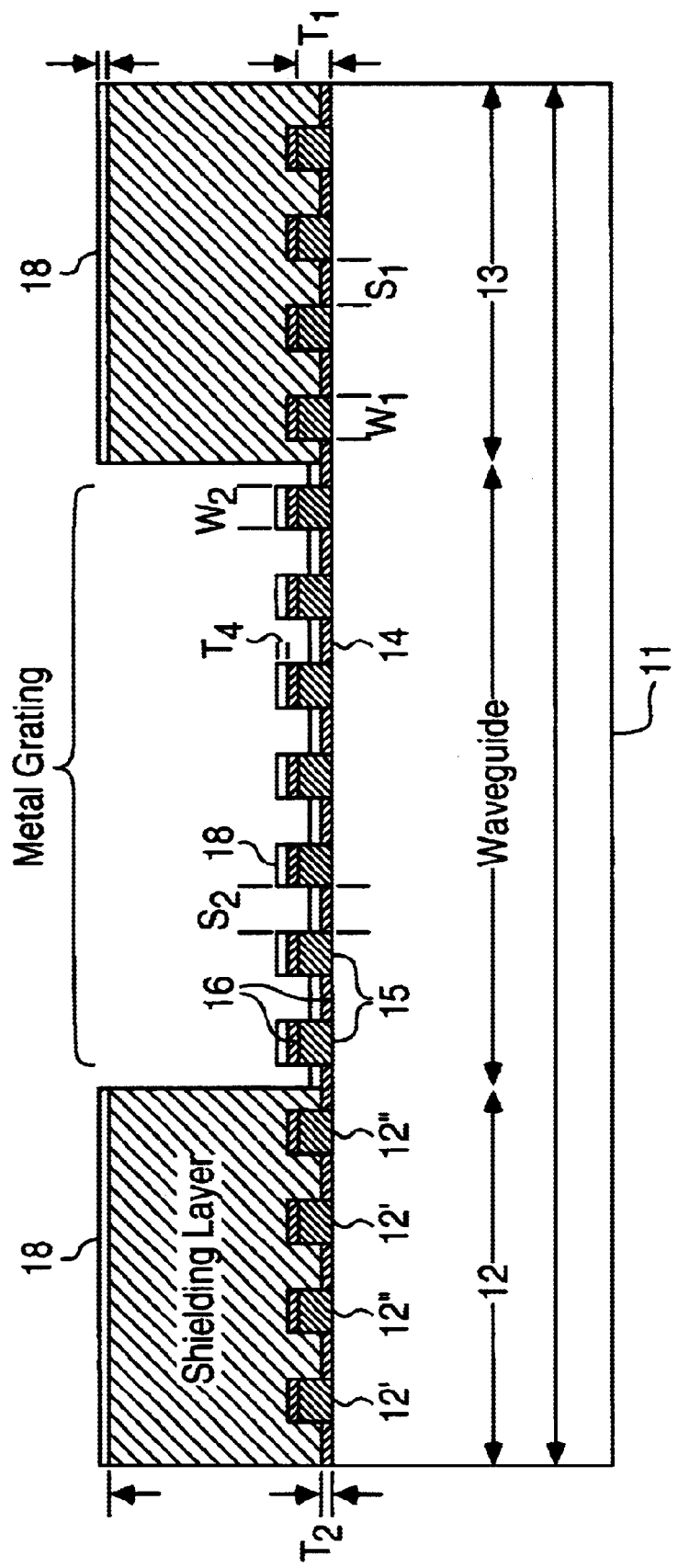
FIG. 1 illustrates in cross-section a surface transverse wave device which may be used in conjunction with the detection method of the invention.

Before the invention is described in detail, it is to be understood that this invention is not limited to specific analytes, coating techniques, sources of flowing liquid streams, or liquid chromatography columns as such may vary. It is also to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a receptor" includes mixtures of two or more such receptors, and the like. In this regard, it is important to note that the techniques of the present invention may be used to quantitate multiple analytes in a flowing liquid stream, e.g., as captured on a piezoelectric surface transverse wave device.

In this specification and in the claims which follow, reference will be made to a number of terms which shall be defined to have the following meanings:

The term "analyte" as used herein is intended to mean a molecular species to be detected, quantitated or both. As noted above, the analytes are bound to a reactive piezoelectric surface which has been coated with an analyte-complementary receptor. The presence or amount of analyte in a sample is determined by virtue of binding the analyte present in the sample to the surface-bound receptor, e.g., an antibody in the case of an antigen analyte. The term "analyte" is also intended to encompass molecular species which are functionally equivalent to analytes of interest in a particular context. For example, in a competitive immunoassay in which the analyte to be quantitated is an antigen which binds to an antibody present in the sample solution, the term "analyte" includes not only the antigen itself but any species which will bind to the antibody in the same manner and with, in general, a similar degree of affinity as the actual antigen. Thus, the term "analyte" includes analyte analogs, analyte fragments, and the like. An analyte may be a ligand, usually an antigen or hapten, an antibody, a single or a plurality of oligosaccharides, analytes which share at least one common epitope or determinant site such as different analytes using a common binding site such as biotin, and the like. An analyte which is recognized by a particular receptor is said to be complementary to that receptor.

The term "receptor" refers to any species which specifically binds to an analyte so as to allow the measurement of the presence or quantity of the analyte. Receptors which recognize a particular analyte are said to be complementary to that analyte. Suitable receptors include, by way of example, antibodies, antibody fragments, antigens, haptens, nucleic acids, particularly single stranded nucleic acids, cells, hormones, binding proteins, oligosaccharides, lectins, avidin, biotin, protein A, protein G, and the like.

A receptor and its complementary analyte are sometimes referred to as a receptor/analyte binding pair. Receptor/analyte binding pairs are well known in the art and include antigen/antibody pairs, biotin/avidin pairs, lectin/oligosaccharide pairs, single stranded nucleic acids and a complementary single or double stranded pair, and the like.

The term "preselected analyte" refers to the analyte complementary to the receptor placed on the surface of the piezoelectric surface wave sample device. The term "piezoelectric surface wave sample device" refers to a piezoelectric surface wave device which contains one or more different receptors bound directly or indirectly to its surface so as to be able to selectively bind one or more analytes complementary to the receptor(s). The receptors are typically attached to the piezoelectric surface wave sample device by covalent bonds, but other types of linkage are possible (e.g., ionic attachment, etc.).

The term "piezoelectric surface wave reference device" refers to a piezoelectric surface wave device whose surface has been derivatized in a manner similar to that of the piezoelectric surface wave sample device but which includes a receptor layer having little or no affinity for the analyte(s) complementary to the receptors found on the surface of the piezoelectric surface wave sample device. Preferably, the piezoelectric surface wave reference device has a binding affinity for the preselected analyte of at least $10^2$, more preferably at least $10^4$, and even more preferably $10^6$ less than binding affinity of the piezoelectric surface wave sample device for the analyte.

Receptors having little or no affinity for an analyte are well known in the art and can be readily obtained by a variety of mechanisms including use of a protein which is not complementary to the preselected analytes. Similarly, chemically altering a nucleic acid strand so that it can no longer bind to its complementary strand is readily achieved by standard chemical procedures. Likewise, the active sites on hormones or other receptors can be chemically altered so as to render them unable to bind to complementary analytes.

Piezoelectric surface wave reference devices containing a receptor layer having little or no affinity for the preselected analyte are effective in reducing physical (temperature, pressure) and chemical (non-specific binding, ionic strength/conductivity/mass density and viscosity) interferences in analyte determinations made by the sample devices by accounting for the shift in resonant frequency not attributable to changes in mass on the surface of the piezoelectric surface wave device.

The term "biotin-binding protein" as used herein is intended to encompass any proteins which will bind to biotin with a $K_a$ of $10^{14}$ L/M or higher. Such proteins include but are not limited to the egg-white protein avidin, a tetramer containing four identical subunits of molecular weight 15,000, and streptavidin, having an almost identical tetrameric structure, whether naturally occurring, recombinantly produced, or chemically synthesized. When the term "avidin" is used herein, it is to be understood that streptavidin and other biotin-binding proteins are intended as well.

The term "alkylene" to denote the preferred structure of the hydrocarbyl moiety linking biotin to the receptor is used in its conventional sense to refer to a bifunctional saturated branched or unbranched hydrocarbon chain containing from 1 to 24 carbon atoms, and includes, for example, methylene ($-CH_2-$), ethylene ($-CH_2-CH_2-$), propylene ($-CH_2-CH_2-CH_2-$), 2-methylpropylene [$-CH_2-CH(CH_3)-CH_2-$], hexylene [$-(CH_2)_6-$] and the like. The term "lower alkylene" refers to an alkylene group of one to six carbon atoms, e.g., methylene, ethylene, propylene, and the like. As will be explained below, the alkylene linking moieties may contain one or more substituents or intervening linking groups which do not interfere with the receptor-biotin complexation.

The term "alkenylene" to denote an alternative structure of the hydrocarbyl moiety linking biotin to the receptor is used in its conventional sense to refer to a bifunctional branched or unbranched hydrocarbon chain containing from 2 to 24 carbon atoms and from 1 to 6, typically 1 or 2, double bonds.

The term "alkynylene" to denote still an additional alternative structure of the hydrocarbyl moiety linking biotin to the receptor is used in its conventional sense to refer to a bifunctional branched or unbranched hydrocarbon chain containing from 2 to 24 carbon atoms and from 1 to 6, typically 1 or 2, triple bonds.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkoxy" as used herein intends an alkyl group bound through a single, terminal ether linkage; that is, an "alkoxy" group may be defined as $-OR$ where R is alkyl as defined above. A "lower alkoxy" group intends an alkoxy group containing one to six, more preferably one to four, carbon atoms.

"Halo" or "halogen" refers to fluoro, chloro, bromo or iodo, and usually relates to halo substitution for a hydrogen atom in an organic compound.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

Methods for attachment of the receptors to the surface of a selected piezoelectric substrate are well known in the art and include by way of example, the use of organic silanes, avidin or streptavidin, biotin, proteins, polymers, lipid bilayers, synthetic coatings, and the like, as disclosed in U.S. Pat. No. 5,306,644, cited above. The specific means for attachment to the piezoelectric surface wave device surface are not critical and any well-known means for attaching a receptor to a solid surface can be used. See, for example, Wong, *Chemistry of Protein Conjugation and Cross-linking*, CRC press, Inc., Boca Raton, Fla., which discloses conventional means for the attachment of a protein receptor to the surface of a solid support.

In one embodiment, the receptor is attached to the surface through a binding layer ("reactive surface layer") attached to the surface of the piezoelectric substrate which includes $SiO_2$ and derivatives of $SiO_2$. See, for example, U.S. patent application Ser. No. 07/404,721. Additionally, when such a reactive surface layer is employed, it coats the surface of the piezoelectric surface wave device including gratings, plates, etc., and, accordingly, shields the surface of the device from undesirable chemical activity.

In this embodiment, the receptor layer can be coupled directly to the reactive surface layer via well-known chemistry (see Wong, supra) or can be bound to a ligand binding layer which, in turn, is coupled to the reactive surface layer. In this latter embodiment, the ligand binding layer acts as a coupling layer between the device surface and the receptor layer (ligand bearing layer).

In one particular embodiment, and by way of example only, the reactive surface layer is formed in a three-step process which first involves the sputter deposition of $SiO_2$ (about 100 to 1000 Å thick and preferably about 500 Å thick) onto the piezoelectric surface wave device surface, resulting in a number of reactive hydroxyl groups on the surface. In the second step, the hydroxyl groups are treated with an organosilane coupling agent to further functionalize the reactive surface layer.

In this regard, the organosilane coupling agent is preferably represented by the formula $R_nSiX_{(4-n)}$ where X represents a hydrolyzable group, for example, alkoxy, acyloxy, amine, chlorine, or the like; R represents a non-hydrolyzable organic radical that possesses functionality which enables the coupling agent to bond with organic resins and polymers, and the like; and n is an integer equal to 1, 2 or 3. On example of such an organosilane coupling agent is 3-glycidoxypropyl-trimethoxysilane (GOPS); the chemistry for using GOPS as a coupling agent is well known in the art. See, for example, Arkins, "Silane Coupling Agent Chemistry," *Petrach Systems Register and Review*, Anderson et al. eds. (1987). Another example of an organosilane coupling agent is (γ-aminopropyl)triethoxysilane. Still, other suitable coupling agents are well known in the art.

In a third step, the organosilane coupling agent (now covalently attached to the surface of the piezoelectric substrate) is bound directly or after derivatization to provide a reactive surface layer on the surface of the piezoelectric surface wave device. As an example of this latter embodiment, if the organosilane coupling agent contains epoxy groups, then these groups can be converted to reactive aldehyde groups by conventional methods (e.g., reaction with sodium periodate) to provide a surface layer on the device which is reactive with amine groups.

The ligand binding layer is then attached by contacting the reactive surface layer with a ligand binding reagent under conditions which permit the ligand binding reagent to strongly bind to the reactive surface layer to form a ligand binding layer. Suitable ligand binding reagents are well known in the art and the only requirement is that the ligand binding reagent contain sufficient functionality so as to both bind to the reactive surface layer and the receptor.

Preferred liqand binding reagents include antibodies, avidin, streptavidin, lectins, etc. In one embodiment, the ligand binding reagent is avidin and the surface reactive layer contains aldehyde groups which then covalently bind to the avidin through the amine groups thereon to form imines (i.e., Schiff bases —N═C<). Reduction of the imine with a suitable reducing agent such as sodium cyanoborohydride at suitable pH provides the amine derivative and results in the covalent attachment of the avidin to the surface layer of the piezoelectric surface wave device. Alternatively, if the organosilane coupling agent provides for surface amino groups, these can then react directly with the carboxyl groups present on the avidin to form covalent amide bonds. In this embodiment, it may be desirable to activate the carboxyl groups of the avidin prior to reaction with the surface amine groups.

After formation of the ligand binding layer, the receptor or ligand bearing layer is formed. This layer is readily formed by contacting the ligand binding layer with a receptor species which is selective for the preselected analyte and which contains further functionality suitable for binding to the ligand binding layer. Methods by which a receptor species can be coupled to a ligand binding layer are well known in the art. Preferred receptor species include antibodies, antigens, etc., which contain amino and carboxyl functionalities allowing them to be bound to the ligand binding layer with minimum loss of activity for the preselected analyte. Other preferred receptor species are biotinylated antibodies or other biotinylated proteins, e.g., protein A or protein G, which become bound to the avidin ligand binding layer by tight biotin/avidin interaction and which are nevertheless selective for the preselected analyte.

As is apparent, the same or different receptors can be bound to the surface of a piezoelectric surface wave device. When the same receptors are employed, the resulting individual device can detect both the presence or quantity, or both, of the preselected analyte. When different receptors are employed, the resulting individual device can detect only the presence of one of the preselected analytes but cannot determine which analyte is present or their concentrations.

Additionally, while the above discloses one method for attaching a receptor layer onto the surface of the piezoelectric surface wave device, other methods are well known in the art including, for example, direct coupling of the receptor to the surface.

Optionally, the surface of the piezoelectric substrate is coated with a layer of a biotin-binding protein to provide a selectively reactive surface. Thus, in the third step described above, the organosilane coupling agent, now covalently bound to the substrate surface, is derivatized to provide for reactive groups which will bind an avidin or streptavidin coating. For example, if the organosilane coupling agent provides for surface vicinal diol groups, these can be converted to reactive aldehyde groups by conventional methods (e.g., by reaction with sodium periodate). The reactive aldehyde groups react with the amino groups in avidin to form imines. The imines are reduced with a suitable reducing agent, as describe above, which results in the covalent attachment of the avidin to the surface layer of the piezoelectric surface wave device.

Still other methods of binding avidin to substrate surfaces are described in Hermanson et al. (1992) *Immobilized Affinity Liqand Techniques*, Academic Press, San Diego, Calif., at pages 199–202. Examples of such other methods include cyanogen bromide and periodate-induced activation of Sepharose, after which avidin can be directly coupled to the activated surface.

In this particular embodiment, after coating the substrate surface with avidin or like biotin-binding protein, a covalent receptor-biotin complex is prepared which will then bind to the avidin-coated surface. Suitable receptors include antibodies, antigens, receptors, ligands, protein A, protein G, lectins, or other receptors with suitable selectivity and specificity for the analyte. The covalent receptor-biotin complex may be represented by the general formula

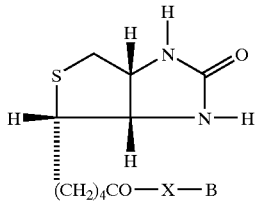

where X is a linking group and B is a receptor. X is typically a $C_1$–$C_{24}$, more typically $C_1$–$C_{12}$, hydrocarbyl linker substituted with 0 to 6, preferably 0 to 4, substituents selected from the group consisting of lower alkyl, lower alkoxy, hydroxyl, halogen and amino, optionally containing 1 to 6, typically 1 to 4, —O—, —S—, —$NR^1$— (where $R^1$ is hydrogen or lower alkyl), —CONH—, —(CO)— or —COO— linkages. Generally, X will have an alkylene backbone, although it may also have an alkenylene or alkynylene structure as defined earlier herein.

It may be necessary to functionalize the receptor so that it is capable of reacting with biotin, i.e., by providing an amino, hydroxyl, carboxyl group, or the like, on the receptor. It will be appreciated that techniques for such functionalizations are well known to those skilled in the art of synthetic organic chemistry. Examples of such techniques are described in co-pending U.S. patent application Ser. No. 08/167,273, cited above.

In general, the receptor is coupled to a biotin molecule which has been activated so that it readily reacts with a functional group on the receptor. A variety of activated biotins are commercially available, e.g., from Pierce Chemical Co., Molecular Probes, Sigma, and Vector Labs.

Methods for coupling biotin to various types of molecules are well known in the art, and the particular method used is not critical. Suitable methods are described, for example, by M. Wilchek et al., in "The Avidin-Biotin Complex in Bioanalytical Applications," *Anal. Biochem.* 171:1–32 (1988).

The covalent receptor-biotin complex is then provided as a coating layer over the ligand binding layer prepared above, i.e., containing a layer of biotin-binding protein. This is done by dissolving the complex in a suitable solvent system. While it will be appreciated by those skilled in the art that any number of solvents or solvent systems may be used, an example of a particularly preferred solvent system is a combination of water and dimethylformamide. The covalent complex is generally dissolved in the minimum amount of organic solvent necessary to effect solution, and then introduced into water (a typical final concentration of covalent complex is approximately 1 wt. %). This solution is then coated to at least monolayer thickness on the ligand binding layer prepared above. The quantity of receptor on the surface is then measured by contacting the substrate surface with a quantitatively detectable analyte, i.e., a molecular species which binds to the receptor through a covalent, ionic, or ligand-receptor bond, or by adsorption. The quantity of receptor present on the surface is then evaluated, e.g., by detection of a label present on the analyte, by determination of the mass of the surface-bound analyte, or the like.

A piezoelectric surface wave device generally comprises a piezoelectric substrate, one or more transducers, typically interdigital transducers (IDTs), and gratings or plates which trap the mode to the surface of the substrate. A grating-based piezoelectric surface wave waveguide or device is known as a surface transverse wave (STW) device, whereas a plate-based piezoelectric surface wave guide or device is known as a Love Wave device. Additionally, for piezoelectric surface wave sample devices, the device includes a chemically reactive layer (receptor layer) to react with the preselected analyte or analytes to be detected. As such, the measurement system is capable of determining the presence or quantity, or both, of an analyte or analytes in a sample, particularly a liquid sample. Such devices are disclosed commonly assigned U.S. Pat. No. 5,130,257, cited above, and illustrated in FIG. 1.

Referring now to FIG. 1, on a piezoelectric substrate 11, such as of quartz or lithium niobate ($LiNbO_3$), are formed an input transducer, such as interdigital transducer (IDT) 12 having electrodes 12' and 12", and an output transducer, such as interdigital transducer (IDT) 13. These IDTs have a typical thickness $T_1$ on the order of 0.1–1.0 microns, a width $W_1$ on the order of 1–100 microns and a spacing $S_1$ on the order of 1–100 microns. Reflective gratings are optionally placed at the outside edge of each IDT. These transducers and gratings can be formed by well-known photolithographic techniques.

In general, the material chosen for substrate 11 must be piezoelectric and have specific crystal cuts that enable trapping of surface transverse waves at a surface of the substrate, and should: (1) exhibit low acoustic loss (i.e., have low viscous attenuation); (2) have a high dielectric constant and high electro-mechanical coupling constant to minimize the parasitic electrical effects of fluid loading upon the transducer; and (3) have a low variation of velocity with temperature. Quartz has the advantage of exhibiting a low temperature variation of the acoustic velocity. Lithium niobate has the advantage of better piezoelectric coupling to IDTs 12 and 13. The ST-cut of quartz (typically used for SAW devices) can be used for STW devices by rotating the propagation direction 90 degrees. On top of surface 14, between IDTs 12 and 13 is formed a metal grating 15 having element width $W_2$ and spacing $S_2$ comparable to the width and spacing of IDTs 12 and 13. This grating traps the transverse acoustic wave to the surface of the substrate. The fingers of the grating can be shorted together with busbars to minimize the dielectric effects of the fluid on the performance of the detector.

An attachment layer 16 can be deposited (e.g., by sputtering or evaporation) on top of elements 12, 13 and 14. Layer 16 should bind strongly and be hermetic to protect elements 11 to 15 from attack by chemicals. This layer has a thickness $T_2$ on the order of 10–1,000 Å, and is selected to provide a good binding surface for the reactive layer 18 of biotin-binding protein, which is then adapted to bind a layer of biotinylated receptor as described herein.

Figure 2:
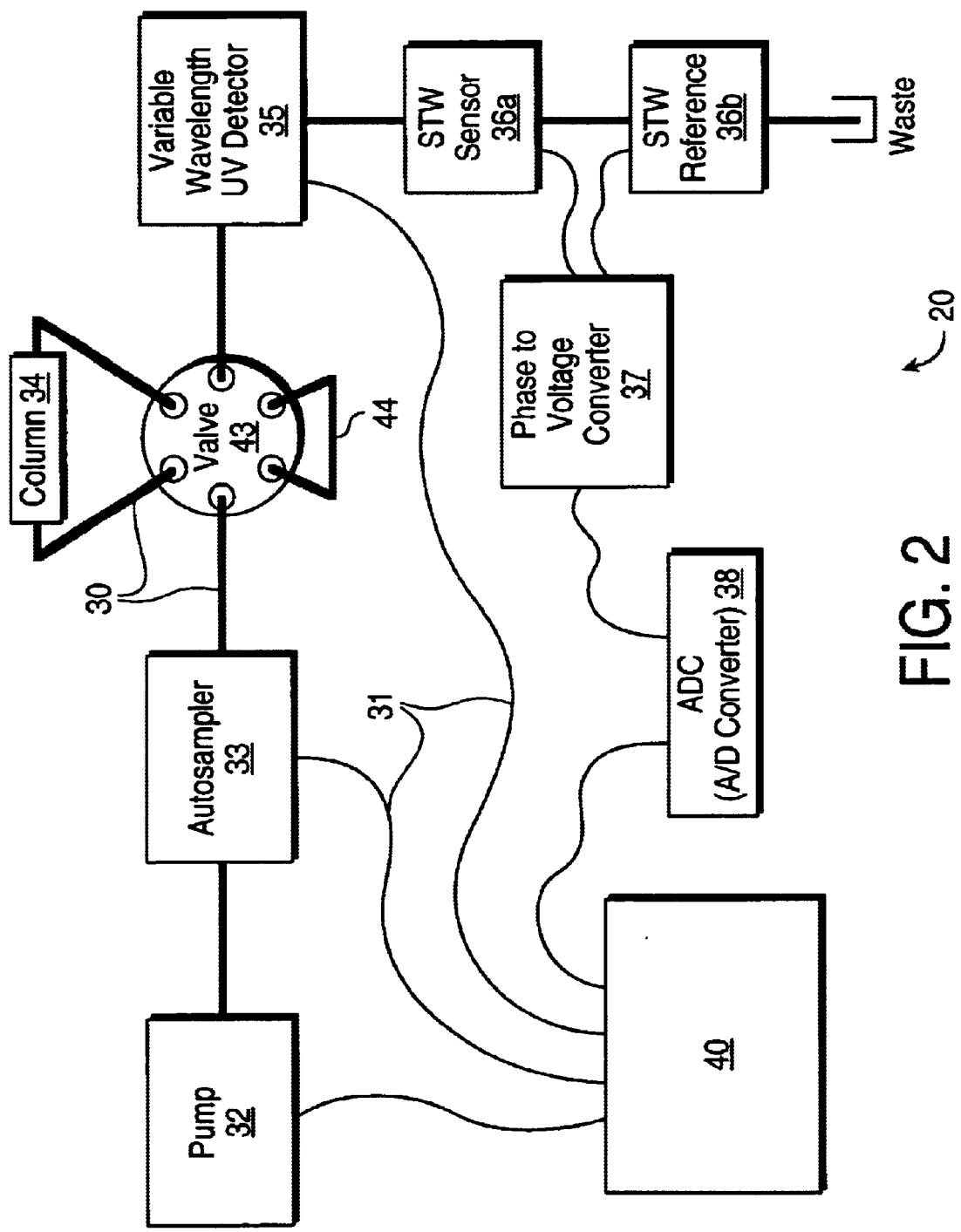
FIG. 2 is a representation of a typical chromatography system which incorporates an STW detector.

An example of a chromatography system in which an STW biosensor is used as a post-column on-line eluant monitor is illustrated in FIG. 2. While FIG. 2 describes the claimed invention in the context of a high performance liquid chromatography (HPLC) system, it will be recognized by those of skill in the art that the context may similarly include other types of liquid chromatography systems, or other systems in which a flowing liquid stream containing a mixture of constituents is processed to separate the constituents so as to increase the purity thereof, for example, filtration, and other techniques in which constituents in a sample are separated for the purpose of purifying the constituents and the product is analyzed for presence and quantity of analyte or analytes by providing a flowing liquid stream, e.g., centrifugation.

Referring now to FIG. 2, the thick lines 30 represent means by which components of the system are in fluid communication with one another. The thin lines 31 represent electrical means of intracomponent communication. A chromatography mobile phase flows by means of a pump 32, or any other suitable motive means, e.g., hydrostatic pressure, through an autosampler 33. Thereafter, the mobile phase is passed through valve 43, or other flow diversion means, onto and through column 34, or other separation means, for example, a filtration means. The flowing liquid stream exits the column as an eluant which is then directed to pass, in turn, through a detection means which, in the present example, comprises UV monitor 35, piezoelectric surface wave sample device 36a and piezoelectric surface wave reference device 36b, and thereafter is directed to waste or other collection means. The electrical signals from the piezoelectric surface wave sample and reference devices are communicated to an interferometer 37 which acts as a phase-to-voltage converter (PVC). The PVC supplies a 250 MHz sine wave at 10 dBm to each piezoelectric surface wave device (sample and reference) and produces a DC output that is proportional to the difference in phase between the signals that return from these devices; the PVC output may be offset by 500 mV to allow measurement of negative-going signals. The output of the PVC is provided to analog-to-digital converter 38, the signal from which is fed to and processed by microprocessor 40. In the embodiment illustrated in FIG. 2, introduction of a sample containing or suspected of containing an analyte of interest onto column 34 is accomplished by way of autosampler 33. Of course, in a gravity-feed or other ambient pressure liquid chromatography system, the sample may be applied directly to the column either automatically or manually, or by way of an alternate flow diversion means. During off-line regeneration of the sample device, the mobile phase is directed to by-pass loop 44 through valve 43, thereby precluding exposure of column 34 to the mobile phase.

The piezoelectric surface wave sample device responds to the chemical environment proximal to the device surface. The reference device provides a means to account for changes in shifts in the resonance frequency which do not correlate to mass changes on the surface of the device due to the presence of the assayed analyte or analytes, i.e., interference. This interference can be removed mathematically so as to provide an accurate calculation of the concentration of the analyte or analytes measured by the sample device or devices.

A system for data acquisition to measure the shift in the resonance frequency or the phase delay from both the piezoelectric surface wave sample device or devices and the reference device or devices is disclosed in U.S. Pat. No. 5,306,644, cited above. Briefly, the system involves the use of multiplexed electronics for launching acoustic waves through each device, means for phase adjustment, mixing and amplification, and means for data acquisition and signal processing to account for the piezoelectric surface wave reference device response.

The flowing liquid stream may be directed to flow over single or multiple piezoelectric surface wave sample devices, for detection of single or multiple analytes, in series or parallel with single or multiple piezoelectric surface wave reference devices. Thus, for example, in a series arrangement, the flowing liquid stream passes first over a sample device and then over a reference device. Alternatively, liquid flow passes in parallel over the sample and reference devices in order to synchronize their exposure cycles and reduce sampling interferences.

A single sample device can be used to measure either for a single analyte (e.g., the sample device contains only one receptor which is complementary to the analyte to be detected) or multiple analytes (e.g., the sample device contains more than one receptor which is complementary to the analytes to be detected). In the former case, the single sample device can provide a quantitative measure of the amount of analyte present. In the latter case, the single sample device can only provide a measure of whether one or more of the preselected analytes is present in the sample fluid but cannot provide a measure of the amount of any one of the analytes.

In another embodiment, multiple sample devices, preferably formed on a single piezoelectric substrate, can be used where each device measures for a separate preselected analyte. In this embodiment, a single sample can be simultaneously screened for the presence and/or quantity of numerous analytes without the need for repetitive measurements.

The piezoelectric surface wave devices may be used once or used repeatedly, with or without periodic refreshment. By periodic refreshment, it is intended that the sample device be regenerated such that it is capable of regaining functional response to the analyte. Regeneration of the device is effected by dissociating the analyte from the receptor. The analyte may be dissociated by a variety of methods including the introduction of chemicals, such as hydrogen ions, hydroxide ions, inorganic salts, organic salts, proteolytic enzymes, proteins, denaturants, or the like, dielectric changes, the application of energy in forms such as heat, light, ultrasound, voltage, or the like, or any combination thereof.

One of the main advantages of using an STW biosensor for liquid chromatography detection is the ability to make continuous measurements, so that the output of the sensor is similar to that of a UV-VIS detector. In contrast to the UV-VIS detector, the STW detector has both selectivity and specificity. For example, as the chromatographic run takes place, eluant passes from the column to the sensor. When the target analyte is present, the sensor will generate a signal that is the integral of the analyte concentration over time. By taking the derivative of the signal one can generate a signal that is related to the amount of compound flowing over the sensor as a function of time. This derivative signal will contain a single peak corresponding to the analyte.

Furthermore, by chemically treating the sensor surface to bind a specific target analyte, the discrimination and selection of the peak of interest can be obtained in real time. The detection method requires no labels or any pre- or post-column derivatization of the sample. The detection system is quantitative and robust as the sensor surface can be repeatedly refreshed. Moreover, the STW detector can make the measurement much faster than an enzyme reactor-detector described above. In general, a measurement with an STW detector -can be made in real time, e.g., within 15 seconds.

The claimed method of detecting an analyte in a liquid chromatography eluant using an on-line biosensor detector eliminates the need to collect fractions and perform extensive biochemical analyses for peak identification. The claimed method also facilitates optimization of methods or procedures for liquid chromatographic separations of target analytes.

While the novel method has been described in conjunction with piezoelectric surface transverse wave devices, it will be appreciated that the method is also useful in conjunction with acoustical, optical, gravimetric, electrochemical, photoelectrochemical, capacitance and thermistor sensors. Gravimetric sensors utilizing piezoelectric crystals include Rayleigh surface acoustic wave devices and Lamb acoustic wave devices as well as the surface transverse wave device. Fiber optic evanescent sensors and evanescent planar waveguide sensors are among the possible optical sensors. Among those in the electrochemical category are potentiometric, amperometric and field-effect transistor ("FET") sensors.

The invention is also useful for measuring a wide variety of analytes. Areas of application include, but are not limited to, environmental sensing, in vitro diagnostics, food and agriculture quality assurance and control, research, and medicine. Examples for use in environmental sensing include the determination of contaminants in natural bodies of water, the evaluation of drinking water quality, determination of pesticides in a water sample, determination of soil and sludge contamination, monitoring of industrial streams, and the like.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

The following examples are put forth so as to provide those of ordinary skill in the art with a complete disclosure and description of how to use the method of the invention, and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXPERIMENTAL

A Hewlett-Packard 1050 Liquid Chromatograph coupled to a variable wavelength detector and an STW biosensor prepared as described below were used in the examples which follow. The column used was a strong cation exchange column (TSK-Gel SP-5PW 07161), 7.5 cm×7.5 cm, having approximately 3 ml of column volume. Solvent A was 20 mM sodium acetate, pH 6.0, and solvent B was solvent A plus 1 M sodium chloride. The flow rate through the column was 1 ml/min.

STW devices were derivatized with an aminosilane and then coupled with the protein avidin D. Protein A with biotin (Vector Labs) was then incubated with the avidin-derivatized device.

After a 45 $\mu$l sample in solvent A was applied to the column, the column was eluted with 100% solvent A for 2 min. Over the following 30 min, the column was eluted with a linear gradient of 100% solvent A to 100% solvent B. For the final 10 min, the column was eluted with 100% solvent B.

The STW sensors were regenerated off-line using 10 mM hydrochloric acid.

EXAMPLES

Liquid Chromatographic Separation and Selective Detection of Human Immunoglobulin G Human immunoglobulin G (HIgG) (Organon-Teknica) in 10% fetal bovine serum (FBS) (Sigma Chemical Co.) was injected onto the HPLC column. FBS was chosen as representative of the cell supernatant or culture medium in which an analyte would be found. A "blank" chromatogram was determined by running the gradient without injecting a sample.

Figure 3A:
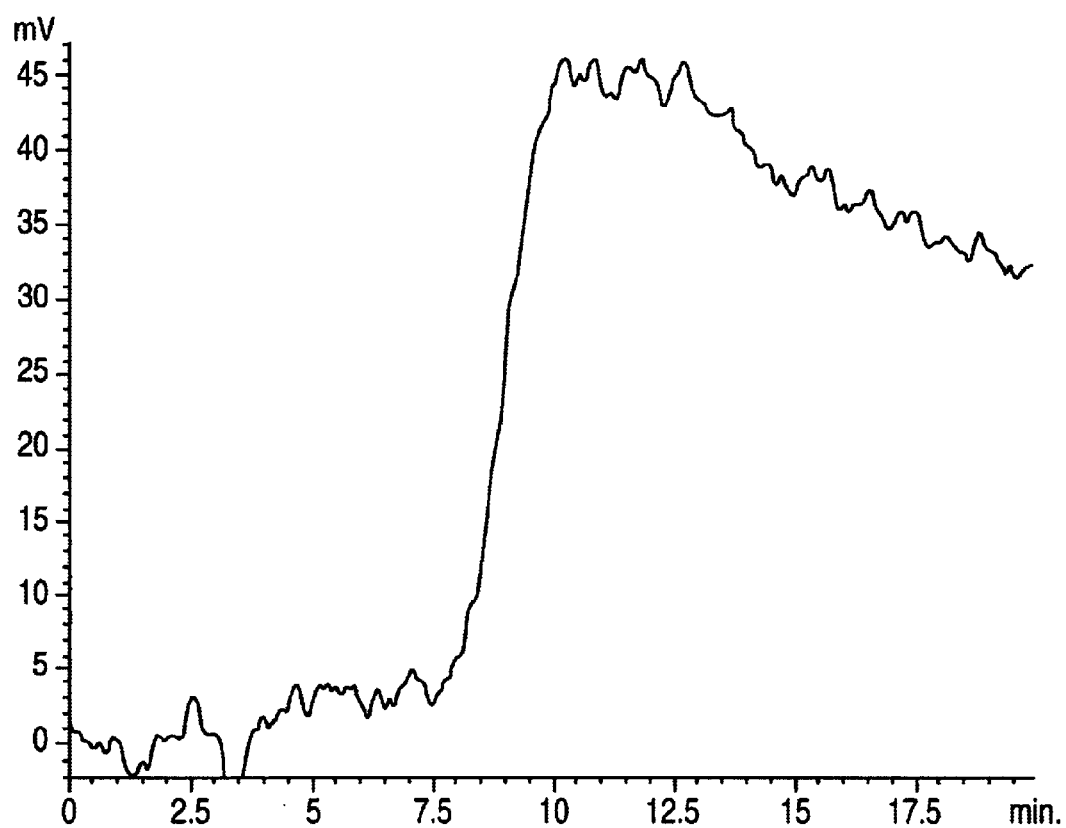
FIGS. 3A–3B.

A. The ability of the STW sensor to detect an analyte in a complex medium was determined by injecting a 45 $\mu$l sample of 1 mg/ml HIgG in 10% FBS onto the HPLC column. The "sensorgram" depicted in FIG. 3a represents the signal from the analog-to-digital converter (ADC) for the sample injection minus the blank. Only the results from the first 20 min of the chromatography run is shown. The increase in the net ADC signal was about 42 mV and the signal-to-noise ratio (S/N) was about 15.

Figure 3B:
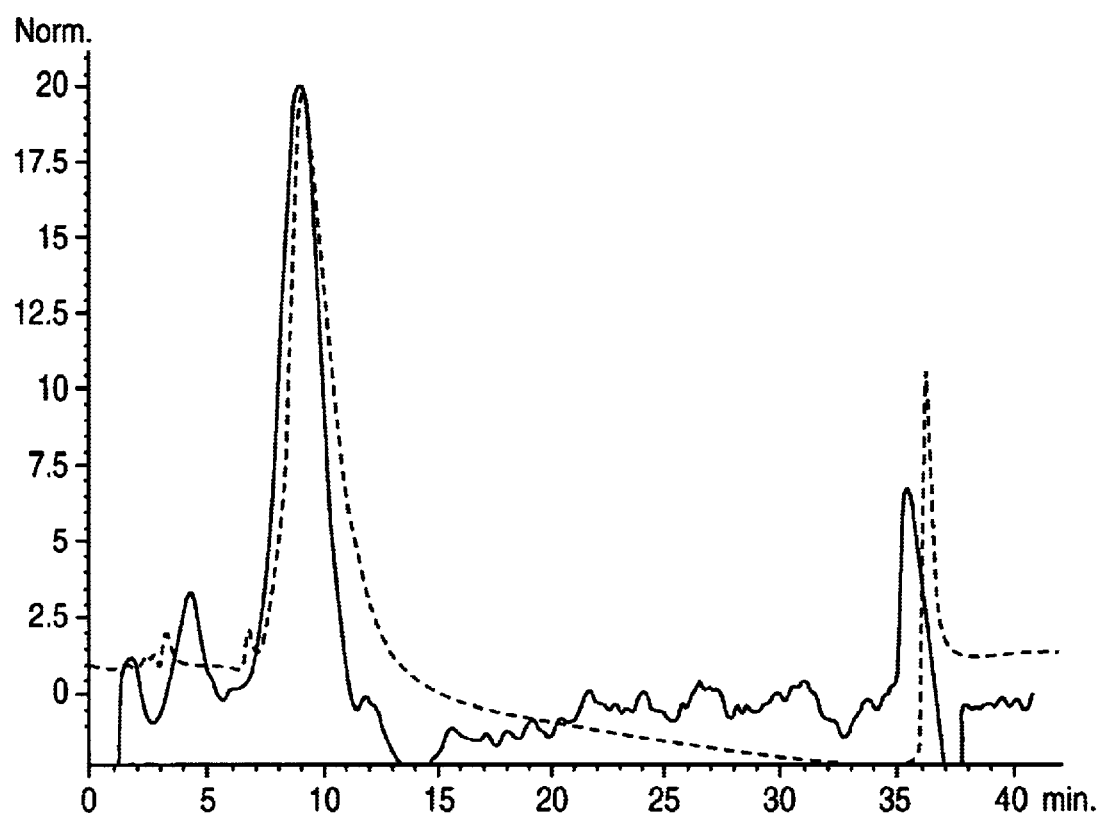
Figure 4A:
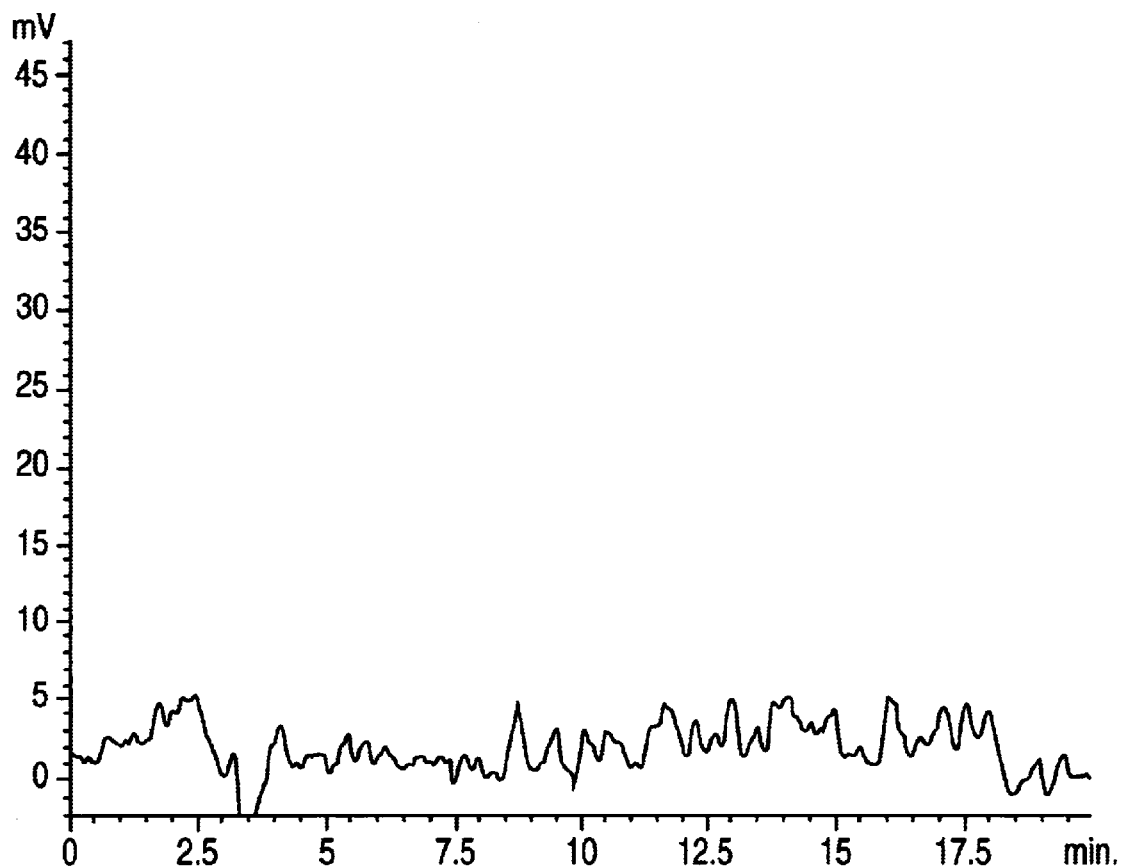
FIGS. 4A–4D.
Figure 4B:
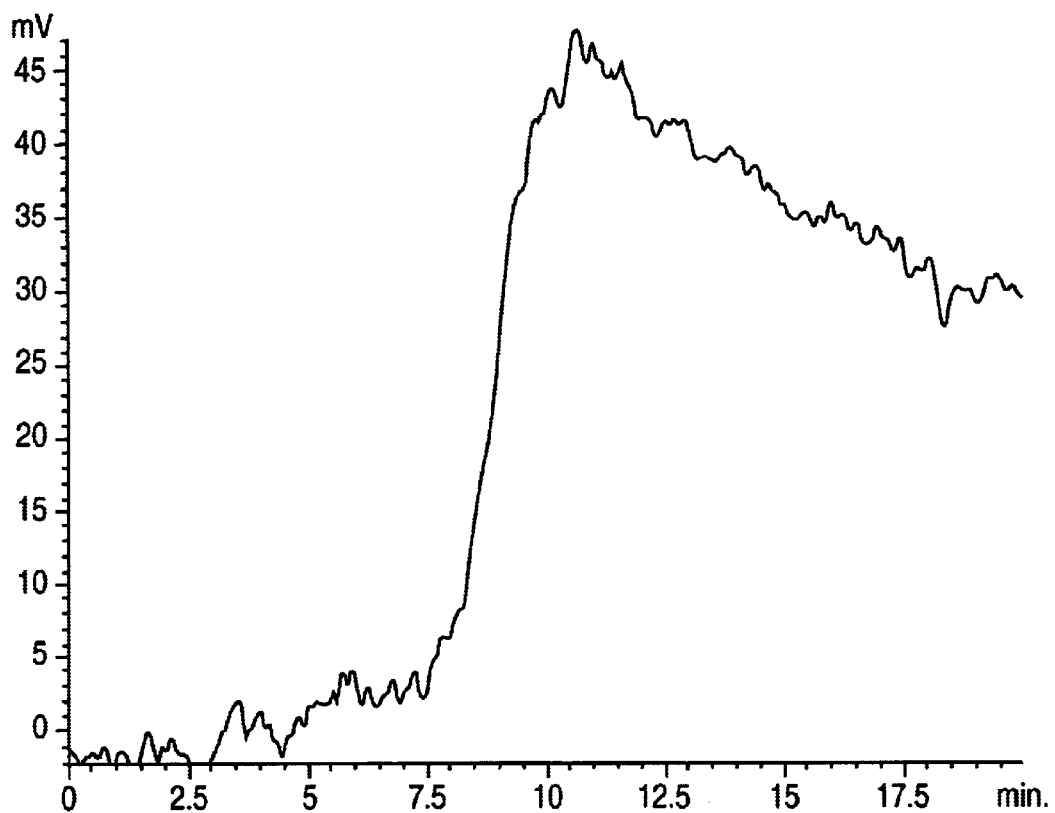
Figure 4C:
Figure 4D:
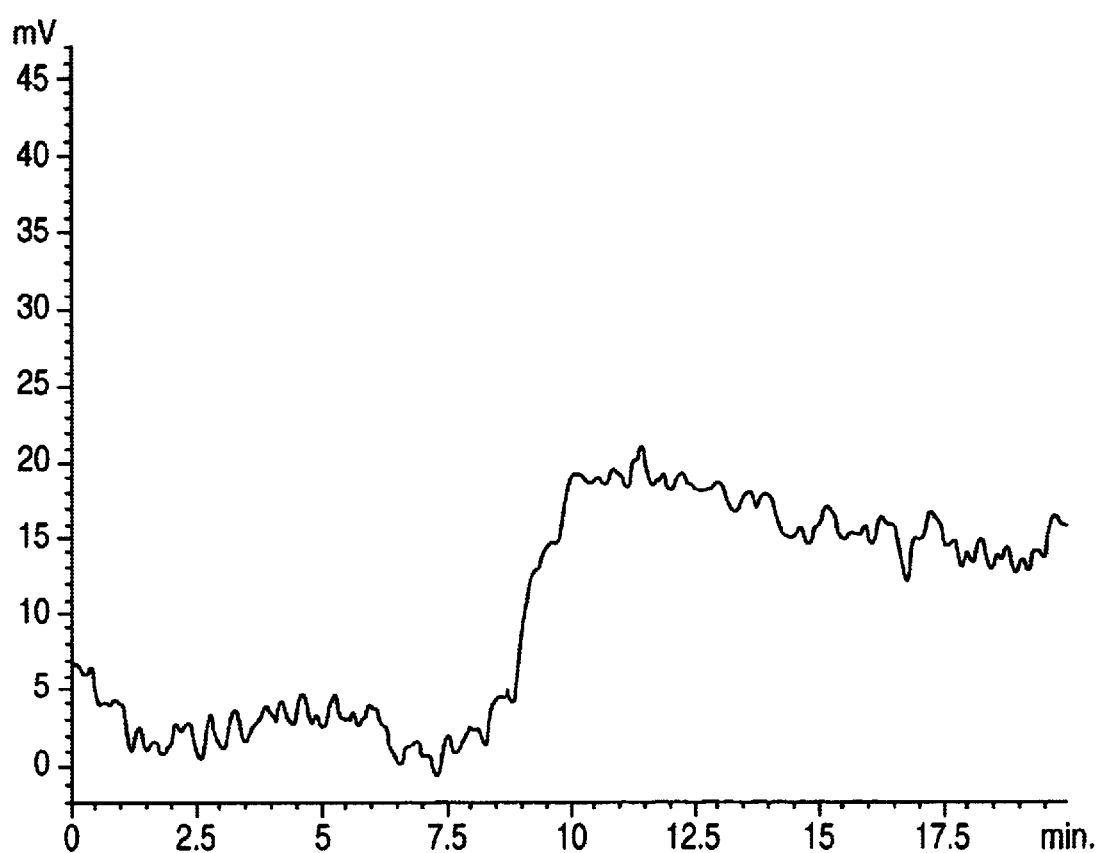

FIG. 3b depicts two overlaid chromatograms: the dashed line is the absorbance at 280 nm and the solid line is the derivative of the signal depicted in FIG. 3a. This experiment demonstrates the ability of the derivatized STW biosensor to detect the analyte in the eluant.

B. The sensitivity range of the STW sensor was determined by applying different concentrations of HIgG, 100 to 1000 $\mu$g/ml, in 10% FBS to the column. The concentration range approximates the possible amounts of HIgG that would be present in cell supernatants. The sensorgrams depicted in FIG. 4 (a) to (d) show the net ADC signal for the sample injection minus the blank for: (a) 10% FBS in 20 mM NaOAc (control); (b) 1 mg/ml HIgG; (c) 500 $\mu$g/ml; and (d) 100 $\mu$g/ml. The sensors were regenerated after each chromatography run in which HIgG was injected onto the column.

Non-specific binding was tested by injecting the 10% FBS only.

The results from these experiments indicate that the STW sensor detects HIgG within this concentration range and, therefore, can be used not only to detect the presence of an analyte in a sample but also to quantitate the amount of analyte therein. Accordingly, the claimed invention is particularly useful in preparative liquid chromatography applications.

We claim:

1. A method for determining the presence or quantity of a preselected analyte in a flowing liquid stream which contains or is suspected of containing the analyte, which method comprises:
   (a) continuously contacting the flowing liquid stream with an on-line system which comprises:
      (i) a piezoelectric surface wave sample device comprising a receptor layer attached to the surface thereof wherein the receptor layer consists essentially of a receptor species complementary to the analyte and which device generates data relating to the mass change on the surface of the device arising from contacting the device with the flowing liquid stream; and
      (ii) a piezoelectric surface wave reference device comprising a receptor layer having little or no affinity for the analyte and which generates data as to the interference arising from contacting the device with the flowing liquid stream;
   (b) continuously obtaining data from both the sample and reference devices; and
   (c) continuously, and contemporaneously with step (a), determining the presence, quantity, or both the presence and quantity of the analyte in the liquid sample.

2. The method of claim 1, wherein the receptor species are selected from the group consisting of antibodies, antibody fragments, antigens, haptens, nucleic acids, cells, hormones, binding proteins, oligosaccharides, lectins, avidin, biotin, protein A and protein G.

3. The method of claim 2, wherein the sample and reference devices each further comprise a surface layer.

4. The method of claim 3, wherein the surface layer is a reactive surface layer derived from one of the group consisting of an organic silane, a protein, a polymer, a lipid bilayer and a synthetic coating.

5. The method of claim 4, wherein the reactive surface layer comprises a protein.

6. The method of 5, wherein the protein is a biotin-binding protein.

7. The method of claim 6, wherein the biotin-binding protein is selected from the group consisting of avidin and streptavidin.

8. The method of claim 7, wherein the receptor species is covalently bound, either directly or indirectly, to biotin, to provide a receptor-biotin complex.

9. The method of claim 8, wherein the receptor is bound directly to the biotin.

10. The method of claim 8, wherein the receptor is bound to the biotin through a linking group.

11. The method of claim 10, wherein the receptor-biotin complex has the structural formula

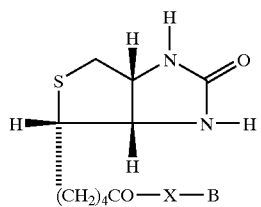

wherein X is the linking group and B is the receptor.

12. The method of claim 11, wherein X is a $C_1$–$C_{24}$ hydrocarbyl linking group substituted with 0 to 6 substituents selected from the group consisting of lower alkyl, lower alkoxy, hydroxyl, halogen and amino, optionally containing 1 to 6 —O—, —S—, —$NR^1$—, —CONH—, —(CO)— or —COO— linkages where $R^1$ is hydrogen or lower alkyl.

13. The method of claim 12, wherein X is a $C_1$–$C_{12}$ alkylene linking group substituted with 0 to 4 substituents selected from the group consisting of lower alkyl, lower alkoxy, hydroxyl, halogen and amino, optionally containing 1 to 4 —O—, —NH—, —CONH— or —(CO)— linkages.

14. A liquid chromatographic system for detecting the presence or quantity of a preselected analyte in a liquid sample comprising a liquid chromatography column in divertable fluid communication with (a) a means for introducing the sample onto the liquid chromatography column, (b) a means for eluting the sample from the column thereby forming an eluant and (c) an on-line detection means in continuous contact with the eluant for continuously and contemporaneously determining the presence, quantity, or both the presence and quantity of the analyte in a flowing liquid stream, which detection means comprises:

(i) a piezoelectric surface wave sample device comprising a receptor layer attached to the surface thereof wherein the receptor layer consists essentially of a receptor species complementary to the analyte and which device generates data relating to the mass change on the surface of the device arising from contacting the device with the flowing liquid stream; and (ii) a piezoelectric surface wave reference device comprising a receptor layer having little or no affinity for the analyte and which generates data as to the interference arising from contacting the device with the flowing liquid stream.

* * * * *